(12) United States Patent
Simonnet et al.

(10) Patent No.: US 8,507,006 B2
(45) Date of Patent: Aug. 13, 2013

(54) POROUS PARTICLES LOADED WITH COSMETICALLY OR PHARMACEUTICALLY ACTIVE COMPOUNDS

(75) Inventors: Jean-Thierry Simonnet, Cachan (FR); Bruno Biatry, Vincennes (FR); Didier Saint-Leger, Courbevoie (FR)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 13/311,080

(22) Filed: Dec. 5, 2011

(65) Prior Publication Data

US 2012/0076841 A1 Mar. 29, 2012

Related U.S. Application Data

(62) Division of application No. 12/285,297, filed on Oct. 1, 2008, now abandoned, which is a division of application No. 10/876,527, filed on Jun. 28, 2004, now abandoned.

(60) Provisional application No. 60/487,245, filed on Jul. 16, 2003.

(30) Foreign Application Priority Data

Jun. 26, 2003 (FR) ..................................... 03 07747

(51) Int. Cl.
*A61K 9/14* (2006.01)
*A61K 8/02* (2006.01)
*A01N 37/36* (2006.01)

(52) U.S. Cl.
USPC ........................... 424/489; 424/401; 514/162

(58) Field of Classification Search
USPC .................................. 424/489, 401; 514/162
See application file for complete search history.

(56) References Cited

U.S. PATENT DOCUMENTS

| 4,690,825 | A | 9/1987 | Won |
| 4,720,489 | A | 1/1988 | Shander |
| 4,885,289 | A | 12/1989 | Breuer et al. |
| 5,035,885 | A | 7/1991 | Arraudeau et al. |
| 5,095,007 | A | 3/1992 | Ahluwalia |
| 5,132,293 | A | 7/1992 | Shander et al. |
| 5,143,925 | A | 9/1992 | Shander et al. |
| 5,328,686 | A | 7/1994 | Shander et al. |
| 5,364,885 | A | 11/1994 | Ahluwalia et al. |

(Continued)

FOREIGN PATENT DOCUMENTS

| EP | 0 285 694 A1 | 10/1987 |
| EP | 0 379 409 A1 | 1/1990 |

(Continued)

OTHER PUBLICATIONS

Sep. 22, 2005 Notice of Reasons for Rejection issued in Japanese Application No. 2004-189843 with English-language translation.

(Continued)

*Primary Examiner* — Aradhana Sasan
(74) *Attorney, Agent, or Firm* — Oliff & Berridge, PLC

(57) ABSTRACT

Individualized porous particles having a volume-average diameter of less than or equal to 10 μm and a specific surface area of greater than or equal to 1 $m^2/g$, and that include at least one cosmetically or pharmaceutically active compound present at least inside the particles.

7 Claims, 1 Drawing Sheet

(56) References Cited

U.S. PATENT DOCUMENTS

| | | |
|---|---|---|
| 5,380,763 A | 1/1995 | Sato et al. |
| 5,411,991 A | 5/1995 | Shander et al. |
| 5,440,090 A | 8/1995 | Davis et al. |
| 5,455,608 A | 10/1995 | Stewart et al. |
| 5,468,476 A | 11/1995 | Ahluwalia et al. |
| 5,475,763 A | 12/1995 | Kaufman et al. |
| 5,614,206 A | 3/1997 | Randolph et al. |
| 5,648,394 A | 7/1997 | Boxall et al. |
| 5,652,273 A | 7/1997 | Henry et al. |
| 5,674,477 A | 10/1997 | Ahluwalia |
| 5,728,736 A | 3/1998 | Shander et al. |
| 5,814,311 A | 9/1998 | Le Bras-Roulier et al. |
| 5,935,587 A | 8/1999 | Cauwet et al. |
| 5,955,109 A | 9/1999 | Won et al. |
| 6,020,006 A | 2/2000 | Styczynski et al. |
| 6,075,052 A | 6/2000 | Suzuki et al. |
| 6,093,324 A | 7/2000 | Bertolini et al. |
| 6,112,794 A | 9/2000 | Hannon et al. |
| 6,120,782 A | 9/2000 | Mansouri |
| 6,139,827 A | 10/2000 | Cohen et al. |
| 6,171,595 B1 | 1/2001 | Suzuki et al. |
| 6,251,411 B1 | 6/2001 | Kishida et al. |
| 6,287,549 B1 | 9/2001 | Sumian et al. |
| 6,355,686 B1 | 3/2002 | Bajor et al. |
| 6,355,687 B1 | 3/2002 | Bajor et al. |
| 6,369,099 B1 | 4/2002 | DeLuca et al. |
| 6,375,948 B1 | 4/2002 | Tsuji et al. |
| 6,387,995 B1 | 5/2002 | Sojka |
| 6,399,652 B1 | 6/2002 | Parks |
| 6,399,774 B1 | 6/2002 | Vasudevan et al. |
| 6,407,056 B1 | 6/2002 | Seiberg et al. |
| 6,586,013 B2 | 7/2003 | Victor |
| 2002/0012645 A1 | 1/2002 | Midha et al. |
| 2002/0176843 A1 | 11/2002 | Creton |
| 2002/0182158 A1* | 12/2002 | Christophides-Lordi et al. ............... 424/64 |
| 2004/0005340 A1 | 1/2004 | Patel et al. |

FOREIGN PATENT DOCUMENTS

| | | |
|---|---|---|
| EP | 0 375 520 A1 | 6/1990 |
| EP | 0 460 923 A2 | 6/1991 |
| EP | 1 192 939 A2 | 4/2002 |
| EP | 1 319 387 A2 | 6/2002 |
| EP | 1 321 136 A1 | 6/2002 |
| EP | 1 219 296 A1 | 7/2002 |
| JP | A-62-215638 | 9/1987 |
| JP | A-63-256126 | 10/1988 |
| JP | A-01-500756 | 3/1989 |
| JP | A-01-131112 | 5/1989 |
| JP | A-02-232264 | 9/1990 |
| JP | A-08-067867 | 3/1996 |
| JP | A-10-310708 | 11/1998 |
| JP | A-11-501629 | 2/1999 |
| JP | A-2001-500529 | 1/2001 |
| JP | A-2001-114790 | 4/2001 |
| JP | A-2002-069851 | 3/2002 |
| JP | A-2002-322019 | 11/2002 |
| WO | WO 91/06277 | 5/1991 |
| WO | WO 94/27563 | 12/1994 |
| WO | WO 94/27586 | 12/1994 |
| WO | WO 98/03149 | 1/1998 |
| WO | WO 99/53904 | 10/1999 |
| WO | WO 00/51551 | 9/2000 |
| WO | WO 01/56556 A2 | 8/2001 |
| WO | WO 02/07674 A2 | 1/2002 |
| WO | WO 02/32392 A1 | 4/2002 |
| WO | WO 02/067889 A2 | 9/2002 |

OTHER PUBLICATIONS

Orgasol, "Ultrafine Polyamide Powder/Cosmetic Powders," ATOCHEM, pp. 1-12 {2002} with English language translation.
Dec. 7, 2009 Office Action issued in U.S. Appl. No. 10/876,527.
Jul. 21, 2010 Office Action issued in U.S. Appl. No. 10/876,527.
Nov. 17, 2010 Office Action issued in U.S. Appl. No. 10/876,527.
Nov. 18, 2010 Office Action issued in U.S. Appl. No. 12/285,297.
Aug. 4, 2011 Office Action issued in U.S. Appl. No. 12/285,297.

* cited by examiner

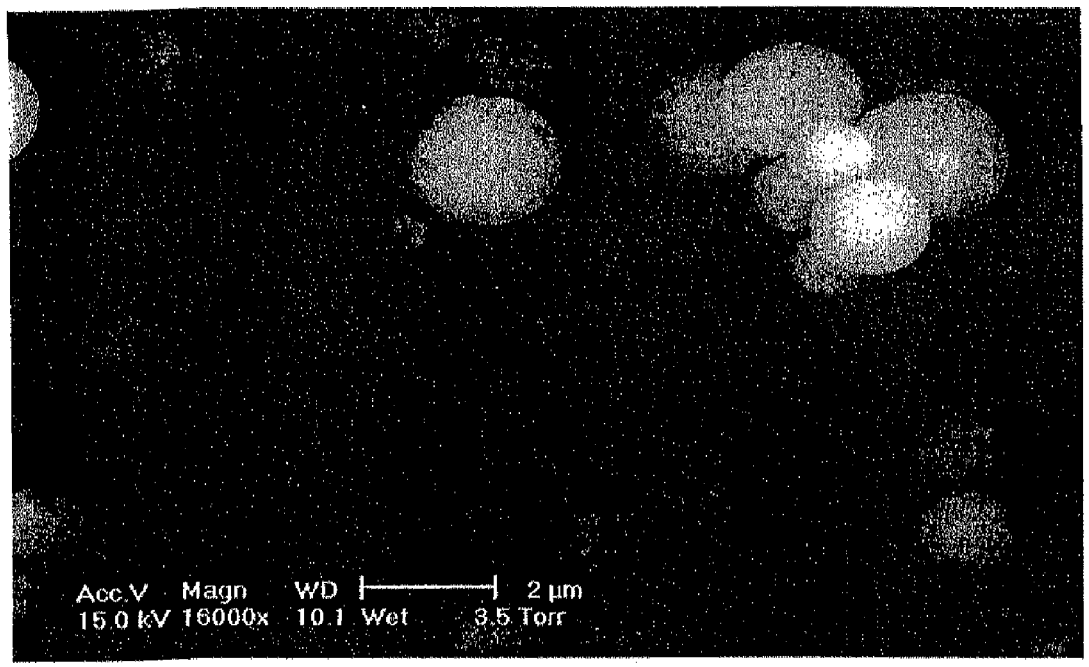

POROUS PARTICLES LOADED WITH COSMETICALLY OR PHARMACEUTICALLY ACTIVE COMPOUNDS

CROSS-REFERENCE TO RELATED APPLICATIONS

This is a Divisional of application Ser. No. 12/285,297, filed Oct. 1, 2008, which is a Divisional of application Ser. No. 10/876,527 filed Jun. 28, 2004 which claims the benefit of French Application No. 03 07747 filed on Jun. 26, 2003 and U.S. Provisional Application No. 60/487,245 filed on Jul. 16, 2003, the entire disclosures of which are hereby incorporated by reference herein in their entirety.

BACKGROUND OF THE INVENTION

The present invention relates to individualized porous particles having a volume-average diameter of 10 µm or less and containing at least one cosmetically or pharmaceutically active compound. The present invention further relates to use of such particles for transporting and releasing an active compound in the pilosebaceous unit.

To increase the efficacy of formulations for topical application, whether they are cosmetic or pharmaceutical in type, certain methods have already been proposed that aim to improve penetration of active molecules into the stratum corneum forming the superficial layer of skin. By way of example, mention may be made of methods using, as vehicles for active molecules, liposomes, nanocapsules, O/W emulsions, short alcohols, glycols, etc.

The pilosebaceous unit forms, within the stratum corneum, the epidermis, the dermis and an invagination comprising a hair follicle and a sebaceous gland. The pilosebaceous unit is a site of considerable biological and enzymatic activity which has a major effect on the appearance of the skin. Among these effects, mention may be made, for example, of the influence of the production of the sebum on the greasy or dry nature of the skin, and the influence of the growth or loss of growth of body hair or head hair on the pilosity of the skin. The pilosebaceous unit can also be the subject of an inflammatory process. Such a process can have various causes and can in particular be related to the presence of microorganisms. This process can result in or contribute to the manifestation of a certain number of skin conditions such as acne. In addition, the pilosebaceous unit constitutes a potential route of passage for agents intended to act on deep skin tissues, such as, for example, agents of the deep anti-wrinkle type, the slimming type, etc.

The structure of this pilosebaceous unit, both by virtue of its morphology with the presence of hair, and by virtue of its physiology with a continuous flow of sebum, naturally opposes the penetration and/or the diffusion of active compounds within and into the depths of the pilosebaceous unit.

However, methods for targeting active compounds into the pilosebaceous unit have already been proposed.

EP 0 375 520 describes the use of microspheres of natural or synthetic polymers or of fatty substances with a melting point above 50° C., loaded at least with an active product, and in which at least 80% by weight of the microspheres are between 3 µm and 10 µm in diameter, for preferentially transporting the active product into the pilosebaceous unit. The microspheres described in that application are either microspheres consisting of crosslinked materials, or solid microspheres loaded by partial solubilization of their constituent materials, and which have a specific surface area of less than 1 m$^2$/g. In addition, the processes for preparing microspheres described in EP 0 375 520, which comprise the encapsulation of the active compound either by means of solvents having sufficient affinity with respect to the material making up the microsphere, or by an "emulsification-evaporation" method, only allow approximate control of the homogeneity of the microspheres obtained. As a result, the microspheres have a low or varied capacity to load the active compound and a low or varied capacity to release the active compound in the pilosebaceous unit.

WO 02/07674 proposes a method for increasing the penetration of an active compound into the pilosebaceous unit using a composition in the form of microspheres or liposomes having the property of being introduced into the follicle and of swelling therein by virtue of subsequently being in contact with a swelling agent, so as to generate a passage into the follicle. However, WO 02/07674 does not provide any concrete example illustrating the proposed method and does not therefore make it possible to verify the effectiveness of the proposed method.

U.S. Pat. No. 6,287,549 describes a method of hair removal using a composition comprising organic microparticles loaded with chromophore agents, in which at least 80% by weight of the microparticles are between 3 and 10 µm in size, in order to transport the chromophore agent into the pilosebaceous unit. These microparticles may be of various types and may be loaded with chromophores either as they are formed, or by impregnation of already formed microcapsules. In these microparticles, the compounds transported are not active compounds as such, since they require the intervention of an outside factor in order to be able to exercise an effect. In addition, exercising of this effect does not require their release from the microparticles. Moreover, U.S. Pat. No. 6,287,549, which explicitly provides for an optional step of application of a composition for solubilizing the chromophores so as to allow their release from the microparticles, does not suggest the possibility of a passive release and even teaches away from such passive release.

U.S. Pat. No. 4,690,825 describes vehicles consisting of porous particles which are between 10 µm and 100 µm in size, for the controlled release of active ingredients. These particles are prepared by copolymerization of monomers based on styrene, vinyl stearate and divinylbenzene or methyl methacrylate and ethylene glycol dimethyl methacrylate, in the presence of a porogen which is also the active ingredient. There is a risk that products so prepared will contain residues from preparation, which are likely to affect the products' innocuousness.

WO 99/53904 describes soft capsules containing an oily suspension or a silicone/polyethylene glycol emulsion and spherical porous microparticles prepared in particular according to U.S. Pat. No. 4,690,825, mentioned above. More precisely, this application describes porous microparticles having a mean particle diameter by weight of 20 µm, loaded either with retinol or with ascorbic acid.

U.S. Pat. No. 6,387,995 describes a process for producing an adsorbent polymer in the form of agglomerated, i.e., non-individualized, microparticles with a very low density ranging from 0.02 g/cm$^3$ to 0.1 g/cm$^3$, capable of trapping lipophilic compounds. The amount of compound trapped in the particles is negligible compared with that of the compound trapped in the space formed by the agglomerated particles.

SUMMARY OF THE INVENTION

It has now been discovered that it is possible to transport at least one active compound and to release the compound in the pilosebaceous unit with increased effectiveness compared to known techniques. Compositions and methods have been discovered that make it possible to improve the encapsulation of an active compound, compared to known compositions and methods, while at the same time exhibiting a particularly satisfactory innocuousness.

The present invention relates to individualized porous particles having a volume-average diameter of 10 μm or less and a specific surface area of 1 m$^2$/g or more. The individualized porous particles include at least one cosmetically or pharmaceutically active compound at least present inside the particles.

The present invention further relates to cosmetic or pharmaceutical compositions including particles as defined above.

For a better understanding of the invention as well as other aspects and further features thereof, reference is made to the following figure and descriptions.

BRIEF DESCRIPTION OF THE FIGURE

Various exemplary embodiments of the invention will be described in detail with reference to the following figure, wherein:

FIG. 1 is an electron micrograph of an exemplary composition according to this invention including silica particles containing triclosan.

DETAILED DESCRIPTION OF EXEMPLARY EMBODIMENTS

The expression "porous particles" refers to particles having a structure containing pores. In particular, a porous structure can allow the incorporation, at least in part, of one or more active agents into particles.

A porous structure may be of a matrix type, like a sponge. A porous structure may also be of a vesicular type, i.e., a particle may have an internal cavity delimited by a porous wall.

The relation of porosity to the size of particles is characterized quantitatively as specific surface area. Exemplary porous particles according to the invention can have a specific surface area, measured according to the BET method, of 1 m$^2$/g or more.

The expression "individualized particles" refers to particles that are not grouped together as an aggregate or an agglomerate. Exemplary individualized particles can have a density of 0.15 g/cm$^3$ or more and, in particular, a density ranging from 0.2 to 5 g/cm$^3$.

The expression "cosmetically or pharmaceutically active compound," as used herein, refers to compounds that, by themselves (i.e., without the action of an outside agent to activate) have biological activity. Often, a compound needs to be in direct contact with its target to exhibit activity.

Exemplary particles according to the present invention can derive from preformed porous particles, i.e., particles formed in the absence of a compound to be encapsulated.

As used herein, the expression "loaded particles" refers to particles, which contain active compound, as distinguished from the particulate material from which they derive.

Exemplary loaded particles according to the invention are substantially free from residues related to the processes for producing particles from which such loaded particles are derived. This characteristic of exemplary loaded particles according to the invention constitutes an improvement in terms of innocuousness compared to particles which, in order to load an active compound, must be formed in the presence of the active compound. Moreover, they are not solid.

Exemplary particles of the invention can be characterized by a high specific surface area, measured by BET.

The BET (BRUNAUER-EMMET-TELLER) method is a method well known to those skilled in the art. It is described, for example in the Journal of the American Chemical Society, 60: 309 (1938), and corresponds to the international standard ISO 5794/1 (annex D). The specific surface area measured according to the BET method corresponds to the total specific surface area, i.e., including the surface area formed by pores.

In various exemplary embodiments, particles according to the invention can have a specific surface area, measured by BET, ranging from 2.5 to 1000 m$^2$/g, in particular from 3 to 750 m$^2$/g, more particularly 300 m$^2$/g or more, or further 500 m$^2$/g or more.

As mentioned above, exemplary particles according to the present invention can have a volume-average diameter of greater than or equal to 10 μm.

In fact, exemplary particles according to the invention can penetrate into a sebaceous follicle by application of a mechanical force. Mechanical force can be applied, for example, by massage. Massage exerts a pushing force and generates a pump effect in a follicle.

Exemplary particles thus gradually reach the follicle canal in which the active compound that they are carrying can then diffuse and, possibly, reach the tissues surrounding the follicle canal. On the other hand, a carrier, which constitutes a particle, can then be discarded by virtue of the flow of sebum and/or the growth of the body hair, thus making it possible to avoid any adverse reaction by the organism with respect to solid compounds constituting particles.

It should be noted that particles having a diameter of greater than 10 μm, even with application of a similar mechanical force, mostly remain located on the surface of the skin without penetrating therein, and can therefore release the active compound only on a cornified layer.

In various exemplary embodiments, particles can have a volume-average diameter of greater than or equal to 0.1 μm, and in particular ranging from 0.5 to 8 μm.

Exemplary particles according to the invention are particles, in particular porous spherical particles, having a number-average size which can range from 0.1 to 50 μm, in particular from 0.1 to 20 μm, and most particularly from 0.5 to 10 μm.

The expression "number-average size" refers to a size given by the statistical mean particle size to half the population, referred to as D50.

In various exemplary embodiments, particles can be characterized by virtue of their particle size homogeneity. In particular, exemplary particles can have a polydispersity index, PI, ranging from 1 to 4, and in particular 3 or less. This polydispersity index is defined as the ratio D(4.3)/D(3.2), in which D(4.3) denotes the volume-average diameter and D(3.2) denotes the surface-average diameter. These two values are commonly measured using laser diffraction particle size measuring devices such as those sold under the name "Mastersizer 2000" by the company MALVERN.

Exemplary porous particles of the invention may have varied shapes, especially globular, and in particular substantially spherical.

Porous particles from which loaded particles according to the invention derive generally consist of materials which are completely insensitive, especially in terms of solubilization and plasticization, to processes for encapsulating active compounds, in particular when such processes employ an organic solvent for impregnation.

Exemplary particles may be of organic, inorganic or mixed type and are most commonly provided in the form of a powder with, in particular, a low volatility.

As porous particles of organic type, mention will be made, by way of example, of Nylon 6, Nylon 6-6, Nylon 12 or Nylon 6-12 particles, such as those sold by the company ATOFINA under the generic name "Orgasol," and particles of poly(methyl methacrylate) (PMMA) such as those sold under the name "Covabead®" by the company WAKER.

In various exemplary embodiments, particles used can be chosen from the nylon particles mentioned above.

In various exemplary embodiments, particles according to the invention can be inorganic in nature.

By way of illustration of inorganic materials which can be used in exemplary particles according to the invention, mention may be made of silica, alumina-silica, hydroxyapatite, titanium dioxide, sericite, mica, magnesium carbonate or hydrocarbonate, aluminium oxides of the alumina type and mixed silicates, such as aluminosilicates, and mixtures thereof.

Exemplary porous mineral particles which may be suitable for the invention, mention may be made of hollow silica microspheres, porous silica microspheres and glass or ceramic microcapsules.

Exemplary porous mineral particles suitable for the invention can be chosen from:

silica particles such as those sold by ASAHI GLASS under the name "Sunsphere H series" and by SUZUKI OIL AND FAT under the name "God Balls", hydroxyapatite particles such as those sold by MERCK (under the reference 1051990010—mean particle size 15 μm), or else those sold by the companies LABORATORY SKIN CARE, ASAHI GLASS and SEKISUI under the respective names "Hydroxyzomes" (LSC and Asahi Glass), AP20C and AP12C (SEKISUI), and "ASP®" by the company SEKISUI PLASTICS.

alumina-silica particles such as those sold under the name "Zeeosphere®" by the company 3M, titanium dioxide particles such as those sold by the company ISHIHARA, and particles made up of a mixture of these minerals.

In various exemplary embodiments, particles can be chosen from silica particles and hydroxyapatite particles.

Exemplary porous particles according to this invention may also consist of organic and/or inorganic composite materials.

Exemplary loaded particles according to this invention can comprise at least one cosmetically or pharmaceutically active compound, the compound being at least present inside the particles. Active compounds can also be present at the surface of loaded particles, but in such a case, the compounds are generally present mostly inside said particles.

In various exemplary embodiments, the ratio by weight of active compound to porous particles not loaded with active compound can be from 1/1000 to 10/1, in particular from 1/100 to 1/1.

Exemplary active agents may include compounds well known to those skilled in the art. Such compounds are generally active agents that are usual in the cosmetics or dermatological field.

Exemplary active compounds may be hydrophilic or lipophilic. In various exemplary embodiments, loaded particles comprise at least one lipophilic active compound. Loaded particles can also comprise at least one hydrophilic active compound, it being possible for the latter to be sufficiently solubilized by amphiphilic compounds present in the sebum to allow its release.

Active compounds considered hereinafter are, without distinction, hydrophilic or lipophilic.

Among exemplary active compounds, mention may in particular be made of:

antibacterial agents such as triclosan, IPBC (iodo-3-propynyl-2-butyl carbamate), benzalkonium chloride, chlorhexidine, totarol® (plant extract comprising totara-8,11,13-trien-13-ol), etc., antifungal agents such as piroctone olamine, zinc pyrithione, climbazole, rilopirox, ketoconazole, itraconazole, etc., sebum regulators such as the iminodibenzyl or fluorene derivatives as described in U.S. Pat. No. 6,355,687, the substituted secondary amine derivatives as described in U.S. Pat. No. 6,355,686, the glucuronic acid and glucosamine derivatives, and their salts, as described in EP 1 219 296, or the combinations of niacinamides with a $C_{11}$-$C_{30}$ alkyl or alkenyl ester of salicylic acid as described in WO 02/067 889, sebum stimulators such as DHEA and its synthetic or natural derivatives, α-hydroxylated derivatives of vitamin D1 such as those described in U.S. Pat. No. 6,369,099, keratolytic agents such as salicylic acid and its derivatives, for instance more particularly 5-n-octanoylsalicylic acid, alpha-hydroxy acids such as those, for example, of glycolic acid, lactic acid or malic acid, and resorcinol, agents for treating acne, such as retinol and its derivatives, retinoic acid and its all-trans or 13-cis isomers, benzoyl peroxide, the cytochrome P450 inhibitors as described in U.S. Pat. No. 6,399,774 and their derivatives, and azelaic acid, antibiotics which may or may not have a macrolide structure, the avermectin compounds as described in U.S. Pat. No. 6,399,652, [(2,4,6-triisopropylphenyl)-acetyl]sulphamic acid 2,6-diisopropylphenyl ester or a salt thereof, as inhibitor of cholesteryl and wax ester synthesis, as described in WO 01/56556, hair loss inhibitors and also hair growth stimulators such as minoxidil, biotin, finasteride, 2,4-dipyrimidine N-oxide, panthenol and their derivatives, flavanone T, or more generally any plant extract, having anti-5-alpha-reductase type 1 or 11 activity, agents which inhibit the growth of head hair or of body hair, such as the serine proteases described in U.S. Pat. No. 6,407,056, cafeic acid, quercetin, propyl gallate, nordihydroguaiaretic acid or NDGA, indomethacin, eflornithine hydrochloride, the plant extracts as described in U.S. Pat. No. 6,171,595, such as the extracts of clove, of rosehip, of burnet, of gambir, etc., the compounds described in U.S. Pat. No. 6,075,052, tetramisole, sodium orthovanadate, levamisole, disodium chromoglycate, vanadium nitrate and gallium nitrate as described in U.S. Pat. No. 6,020,006, and also the compounds described in U.S. Pat. Nos. 4,885,289, 4,720,489, 5,132,293, 5,096,911, 5,095,007, 5,143,925, 5,328,686, 5,440,090, 5,364,885, 5,411,991, 5,648,394, 5,468,476, 5,475,763, 5,455,608, 5,674,477, 5,728,736 and 5,652,273 and in WO 94/27586, WO 94/27563 and WO 98/03149. Use may also be made of the extracts of juniper as described in U.S. Pat. No. 6,375,948, anti-dandruff agents such as zinc pyrithione, antioxidants such as butylhydroxytoluene (BHT), carotenoids such as β-carotene, lycopene, canthaxanthine, ubiquinone, dibutylpentaerythrityl hydroxycinnamate, vitamin E, trolox, vitamin C and its derivatives, astringents and pore-reducing agents, such as those described in WO 02/32392, antiperspirant agents such as aluminium salts and zirconium salts, vitamins, other than those mentioned above, and such as vitamin B3, vitamin K, vitamin H, vitamin PP, vitamin D, vitamin B6 and their derivatives, and anti-inflammatory agents such as α-bisabolol, dipotassium glycyrrhizinate, glycyrrhetinic acid and its derivatives, ellagic acid, ursolic acid, ibuprofen, naproxen, fenoprofen, carprofen, ketoprofen, steroidal anti-inflammatory agents such as cortisone, pregnenolone, desonide, and mixtures of alkolamines and of tyrosine, such as those described in EP 1 192 939.

Mention may in particular be made of all the active agents known for their activity on skin ageing, such as keratolytic or prodesquamating agents, for example α-hydroxy acids, β-hydroxy acids, α-keto acids, β-keto acids, retinoids and their esters, retinal, retinoic acid and its derivatives.

Mention may also be made of vitamins such as vitamins C, B3 or PP, B5, E, K1, and the derivatives of these vitamins, and in particular their esters; free-radical scavengers; DHEA and its derivatives; coenzyme Q10; bleaching and depigmenting agents such as kojic acid, para-aminophenol derivatives, arbutin and their derivatives, and mixtures thereof.

Mention may also be made of active agents that are useful for oily skin, such as zinc salts, and in particular zinc gluconate; antibacterial agents such as salicylic acid, triclosan, lipacide, extract of clove, octopirox, hexamidine; anti-acne active agents.

Amounts of active agents introduced into particles depends on a desired effect. Active agents may be present in the porous particles in an amount of active material ranging from 1 to 50% by weight, especially from 2 to 40% by weight, and in particular ranging from 5 to 30% by weight, relative to the total weight of the particles once loaded.

Exemplary loaded particles according to the invention can be prepared according to conventional methods, in particular by impregnation.

In particular, loaded particles according to the invention can be obtained by impregnation of preformed porous particles with at least one active compound. Advantageously, this protocol does not require the presence of a porogen.

By way of example, impregnation processes can include presolubilizing compounds to be encapsulated in a solvent which is suitable and in an amount necessary and sufficient to impregnate the particles, and bringing a resulting mixture into contact with porous particles according to the invention. Solvent is then evaporated off until a dry powder is obtained. A resulting powder generally contains only a very small proportion of residual solvent, of the order of 1/10 ppm.

As solvents which may be used in such an impregnation process, mention may in particular be made of acetone, ethanol, isopropanol, dichloromethane, ethyl acetate, etc. Of course, the choice of solvent is made taking into account the nature of the components of porous particles and of compounds to be encapsulated.

When compounds to be encapsulated are in the form of liquids, they may be brought directly into contact with porous particles without the addition of a secondary solvent.

Those skilled in the art will be capable of selecting impregnation conditions so as to obtain a dry powder.

Exemplary loaded particles of the invention allow specific administration of cosmetically or pharmaceutically active compounds into the pilosebaceous unit.

Particles can be introduced in various cosmetic or pharmaceutical formulations intended for topical application.

The present invention therefore also relates to cosmetic or pharmaceutical compositions comprising loaded particles such as described above.

Of course, compositions may comprise only one type of particles as described above, or else may comprise a mixture of such particles.

Generally, exemplary compositions contain from 0.1 to 50% by weight, and in particular from 0.2 to 20% by weight, of particles as relative to the total weight of such compositions.

Exemplary compositions according to the invention may also comprise:

at least one cosmetically or pharmaceutically active compound intended to act essentially outside the pilosebaceous unit, and/or at least one cosmetically or pharmaceutically acceptable additive, and/or a galenic carrier, which may be of any suitable type.

The term "carrier" refers to any mode of vehicle compatible with cosmetic or pharmaceutical use, namely of liquid type such as water, an aqueous-alcoholic solvent, oil, or a mixture thereof, or of solid type such as wax for example.

Care will, however, be taken to ensure that with optional additional cosmetically or pharmaceutically active compounds, such optional additives and carriers do not cause the release of active compounds in compositions.

Exemplary compositions according to the invention may also contain conventional adjuvants such as dyes, pigments, fragrances, preserving agents, physical and chemical sunscreens, sequestering agents, liposoluble or water-soluble active agents, moisturizers such as polyols and in particular glycerol, pH adjusters (acids or bases).

In various exemplary embodiments, compositions of the invention are substantially free of surfactants.

Exemplary cosmetic or pharmaceutical compositions may be provided in the form of lotions, O/W or W/O emulsions, or aqueous or aqueous-alcoholic gels, or alternatively in anhydrous form, such as sticks, sprays or compact or free powders.

Exemplary compositions of the invention may be care compositions, hygiene compositions or makeup compositions for the skin of the body or face, or for the keratinous materials such as the nails, the eyelashes, the eyebrows or the hair.

Exemplary compositions may also be employed, for example, for use on the hair and may in particular be shampoos, conditioners, hair lotions, in particular for hair care.

Exemplary compositions compositions may also be makeup-removing products, in particular oils, gels, or makeup-removing or foaming lotions.

Exemplary compositions may also be makeup sticks such as lipsticks, or personal hygiene sticks such as deodorants.

Exemplary compositions may also be makeup products, in particular of the foundation, tinted cream, mascara or eyeliner types.

This invention is illustrated by the following Examples, which are merely for the purpose of illustration.

EXAMPLE 1

Preparation of Mineral Particles Containing an Active Compound and a formulation in a cosmetic composition.

A solution containing 20 g of salicylic acid, 1 l of acetone and 200 g of porous silicas (Sunsphere 1-133) is prepared. This solution is kept at ambient temperature, with stirring, until the active agent is completely dissolved. The solution is then transferred into a round-bottomed flask and the acetone is evaporated off in a rotary evaporator at 40° C. After complete evaporation of the solvent, a powder consisting of porous silica particles, the pores of which comprise salicylic acid in solid form, is thus obtained. The composition by weight of the particles obtained is 10% by weight of salicylic acid and 90% by weight of silica relative to the total weight of the particles.

Cosmetic compositions containing the particles according to the invention are formulated.

| Matting free powder | Control composition (% by weight) | Composition according to the invention (% by weight) |
|---|---|---|
| Talc | 87 | 69 |
| Salicylic acid | 2 | — |
| Dimethicone | 7.5 | 7.5 |
| Magnesium stearate | 2.5 | 2.5 |
| Particles according to the invention (10% salicylic acid-90% silica) | — | 20 |
| Preserving agents | 1 | 1 |

The stability of the composition according to the invention, i.e., comprising 20% of particles according to the invention, is evaluated in comparison to a control composition not containing particles in accordance with the invention. The powders are packaged in a 10 g box. The boxes are then placed, for a period of 2 months, in an incubator with a relative humidity set at a value of 80% and the temperature set at the value of 45° C. The macroscopic appearance of the powders after storage in the incubator is then optically evaluated. The results are given in the table below:

| Composition | Control | According to the invention |
|---|---|---|
| Appearance | Pinkish powder, showing dark pink marks | White powder showing no coloration at the surface or in the mass |

These results show that, after prolonged storage in a humid atmosphere, the composition according to the invention shows no unattractive coloration.

EXAMPLE 2

Two compositions containing a lipophilic active compound, 5-n-octanoylsalicylic acid, namely respectively a gel containing 4 μm porous particles of nylon ("Orgasol®"), which is the subject of the invention, and an O/W emulsion with the same mean particle size are compared in terms of pilosebaceous unit-targeting effectiveness. The amount of active principle, 5-n-octanoylsalicylic acid, is identical in the two types of composition, and is set at 0.3% by weight.

Composition 1 (According to the Invention)

| | |
|---|---|
| Poly(ammonium acryloyldimethyltaurate) | 0.50 g |
| Porous particles of Nylon-12* | 4.70 g |
| 5-n-octanoylsalicylic acid | 0.30 g |
| Poloxamer 338 | 0.25 g |
| Demineralized water | 94.25 g |

The porous particles of Nylon-12 are sold under the name "Orgasol 2002 UD Nat cos" by the company ATOFINA.

Composition 2 (Comparative O/W Emulsion)

| | |
|---|---|
| Xanthan gum | 0.10 g |
| Glyceryl stearate | 1.00 g |
| Sodium hydroxide | 0.10 g |
| Cetyl alcohol | 2.00 g |
| Octyldodecanol | 9.00 g |
| Glycerol | 3.00 g |
| Hydrogenated polyisobutene | 2.00 g |
| Water | 71.95 g |
| 5-n-Octanoylsalicylic acid | 0.30 g |
| Paraffin oil | 5.00 g |
| Carbomer | 0.30 g |
| PEG-100 stearate | 1.00 g |
| Polysorbate 60 | 4.00 g |
| Methylparaben | 0.25 g |

The study is carried out on eight volunteer individuals who have oily skin exhibiting dilated pores on the forehead.

For each individual, after having carefully cleaned the face with soap, 4 mg/cm$^2$ of the composition to be tested are applied to the left or right side half of the forehead, and the area treated is then massaged for 1 minute and left to dry for 15 minutes. This application is repeated for 4 days under the same conditions (i.e., a total treatment period of 5 days with a single daily application).

On day 6, an epidermal sample is taken from each individual by cyanoacrylate strip, by applying onto the forehead of each individual a glass slide onto which a drop of cyanoacrylate has been deposited, and then, after drying, removing the slide, which thus entrains an epidermal sample.

The follicles and the comedones are then removed from the samples and their content is extracted in methanol. The amount of active compound is quantified by HPLC.

The results are presented below.

| | Number of comedones | | 5-n-Octanoylsalicylic acid in pg per comedone | | |
|---|---|---|---|---|---|
| Testers | Area composition 2 | Area composition 1 | Area composition 2 | Area composition 1 | Enrichment |
| 1 | 29 | 34 | 439 | 656 | 50% |
| 2 | 20 | 16 | 282 | 566 | 101% |
| 3 | 25 | 27 | 121 | 200 | 66% |
| 4 | 30 | 33 | 709 | 1288 | 82% |
| 5 | 24 | 13 | 571 | 986 | 73% |
| 6 | 29 | 19 | 468 | 836 | 79% |
| 7 | 11 | 13 | 57 | 259 | 353% |
| 8 | 28 | 25 | 144 | 433 | 201% |

It is noted, according to the results set out above, that composition 1 according to the invention, which contains the porous particles loaded with 5-n-octanoylsalicylic acid, makes it possible to significantly increase the amount of 5-n-octanoylsalicylic acid in the follicle by a rate of at least 50%, compared with a composition in the form of an emulsion containing the same amount of 5-n-octanoylsalicylic acid.

This trial shows the effectiveness of the porous particles of the invention for transporting active molecules into the pilosebaceous unit.

EXAMPLE 3

Preparation of the organic particles containing an active compound.

Particle Composition

| | |
|---|---|
| Porous particles of Nylon-12, sold under the name "Orgasol 2002 UD Nat Cos" ® by the company ATOFINA | 7.5 g |
| Triclosan | 2.5 g |

2.5 g of triclosan are solubilized in 50 ml of acetone. 7.5 g of "Orgasol®" are introduced into this mixture. The dispersion is then introduced into a rotary evaporator in order to eliminate the acetone. A powder loaded with triclosan is then obtained.

The powder thus obtained can then be redispersed in water, in a gel or in an emulsion. Care will be taken to ensure that the composition into which the particles containing the triclosan are introduced does not promote leaking of the triclosan into the galenic carrier.

EXAMPLE 4

Preparation of Organic Particles Containing an Active Compound.
Particle Composition

| | |
|---|---|
| Porous particles of silica sold under the name "God Balls2 EC ®" by the company SUZUKI OILS & FATS | 7.5 g |
| Vitamin E | 1.5 g |
| 5-n-Octanoylsalicylic acid | 1.0 g |

1.5 g of vitamin E and 1 g of 5-n-octanoylsalicylic acid are solubilized in 50 ml of acetone. 7.5 g of "God Balls 2 EC®" porous particles are introduced into this mixture. The dispersion is then introduced into a rotary evaporator in order to eliminate the acetone. A powder loaded with vitamin E and with 5-n-octanoylsalicylic acid is then obtained.

The powder thus obtained can then be redispersed in water, in a gel or in an emulsion. Care will, however, be taken to ensure that the composition into which the particles containing the vitamin E and the 5-n-octanoylsalicylic acid are introduced does not promote leaking of these active agents into the galenic carrier.

Similarly, a powder of particles is prepared with 7.5 g of "God Balls 2 EC®" porous particles and 2.5 g of triclosan. The powder is observed under an electron microscope. A micrograph thereof is shown in FIG. 1.

It is noted that the powder thus obtained consists of individualized particles.

EXAMPLE 5

Preparation of Anti-Acne Cream (Oil/Water Emulsion).

| | |
|---|---|
| Poly(ammonium acryloyldimethyltaurate) | 0.40 g |
| Xanthan gum | 0.20 g |
| Preserving agents | 0.80 g |
| Disodium EDTA | 0.05 g |
| Glycerol | 5.00 g |
| Demineralized water | 75.04 g |
| Porous particles according to Example 3 | 23.00 g |
| Mixture of cetearyl alcohol/dimyristyl tartrate/ C12-15 Pareth-7/PPG-25-Laureth-25 | 1.50 g |
| Stearyl alcohol | 1.00 g |
| Mixture of glyceryl stearate/PEG-100 stearate | 2.00 g |
| Cyclohexasiloxane | 10.00 g |

-continued

| | |
|---|---|
| Ethylhexyl methoxycinnamate | 1.00 g |
| Fragrance | 0.01 g |

This smooth and fresh cream makes it possible to combat problems of acne with good effectiveness.

EXAMPLE 6

Preparation of tonic lotion.

| | |
|---|---|
| Butylene glycol | 1.00 g |
| Zinc oxide | 0.50 g |
| Lactic acid | 0.10 g |
| Glycerol | 1.00 g |
| Propylene glycol | 0.20 g |
| PEG-60 hydrogenated castor oil | 0.15 g |
| Ethanol | 5.00 g |
| 30 nm colloidal silica | 0.50 g |
| Porous particles according to Example 3 | 1.00 g |
| Demineralized water | 90.33 g |
| Extract of *Hamamelis virginiana* | 0.0002 g |
| Menthoxypropanediol | 0.01 g |
| Methylparaben | 0.20 g |
| Fragrance | 0.01 g |

EXAMPLE 7

Preparation of W/O emulsion.
Phase A

| | |
|---|---|
| Isohexadecane | 8.00 g |
| Squalane | 3.70 g |
| Polydimethylsiloxane (viscosity: 10 cst) | 4.10 g |
| Apricot kernel oils | 2.30 g |
| Lubrizol 5603 | 1.90 g |

Phase B

| | |
|---|---|
| Ascorbic acid | 2.00 g |
| 50% potassium hydroxide | 1.20 g |
| Demineralized water | 67.80 g |
| Glycerol | 5.00 g |
| Preserving agents | 1.00 g |

Phase C

| | |
|---|---|
| Particles according to Example 3 | 3.00 g |

Phase B is emulsified slowly, at ambient temperature, in phase A, and then phase C is added.

While this invention has been described in conjunction with the exemplary embodiments and examples outlined above, various alternatives, modifications, variations, improvements and/or substantial equivalents, whether known or that are or may be presently unforeseen, may become apparent to those having at least ordinary skill in the art. Accordingly, the exemplary embodiments of the invention, as set forth above, are intended to be illustrative, not limiting. Various changes may be made without departing from the spirit and scope of the invention. Therefore, the invention is intended to embrace all known or later developed alternatives, modifications, variations, improvements and/or substantial equivalents.

What is claimed is:

1. A method for administering a cosmetically active compound into a pilosebaceous unit, the method comprising:
   topically applying on the surface of skin individualized porous particles or a cosmetic composition including said particles, said particles
   comprising organic porous particles of Nylon 12,
   having a volume-average diameter of less than 10 um and a specific surface area of greater than or equal to 1 $m^2/g$, and
   comprising at least 5-n-octanoylsalicylic acid as the cosmetically active compound present inside said particles.

2. The method according to claim 1, wherein the individualized porous particles have a mass by volume ranging from 0.2 to 5 $g/cm^3$.

3. The method according to claim 1, wherein the individualized porous particles have a polydispersity index less than or equal to 3.

4. The method according to claim 1, wherein the active compound is present in the porous particles in an amount of active material ranging from 5 to 30% by weight relative to a total weight of the particles once loaded.

5. The method according to claim 1, wherein said particles further comprise another cosmetically active compound selected from the group consisting of:

antibacterial agents selected from triclosan, IPBC (iodo-3-propynyl-2-butyl carbamate), benzalkonium chloride, chlorhexidine, and a plant extract comprising totara-8,11,13-trine-13-ol;
   benzoyl peroxide;
   antioxidants selected from butylhydroxytoluene (BHT), β-carotene, lycopene, canthaxanthine, ubiquinone, dibutylpentaerythrityl hydroxycinnamate, vitamin E and its derivatives, trolox, and vitamin C and its derivatives;
   anti-inflammatory agents selected from α-bisabolol, dipotassium glycyrrhizinate, glycyrrhetinic acid and its derivatives, ellagic acid, and ursolic acid; and
   mixtures thereof.

6. The method according to claim 5, wherein the another cosmetically active compound is selected from the plant extract comprising totara-8,11,13-trien-13-ol, vitamin E and its derivatives, glycyrrhetinic acid and its derivatives, and mixtures thereof.

7. A cosmetic treatment method for preventing and/or treating oily skin, comprising topically applying, on the surface of skin of an individual in need thereof, individualized porous particles or a cosmetic composition including said particles, said particles
   comprising organic porous particles of Nylon 12,
   having a volume-average diameter of less than 10 um and a specific surface area of greater than or equal to 1 $m^2/g$, and
   comprising at least 5-n-octanoylsalicylic acid as the cosmetically active compound present inside said particles.

* * * * *